United States Patent [19]

Spencer

[11] Patent Number: 4,871,551
[45] Date of Patent: Oct. 3, 1989

[54] PIGMENTATION SUPPLEMENTS FOR ANIMAL FEED COMPOSITIONS

[75] Inventor: Kenneth G. Spencer, Poway, Calif.

[73] Assignee: Microbio Resources, Inc., San Diego, Calif.

[21] Appl. No.: 153,308

[22] Filed: Feb. 8, 1988

[51] Int. Cl.$^4$ ............................................. A23K 1/00
[52] U.S. Cl. ........................................ 426/2; 426/310; 426/429; 426/518; 426/524; 426/540; 426/541; 426/807
[58] Field of Search ................... 426/310, 807, 2, 250, 426/540, 429, 518, 524, 541; 47/1.4; 241/17

[56] References Cited

U.S. PATENT DOCUMENTS

| | | | |
|---|---|---|---|
| 2,583,697 | 1/1952 | Hendry et al. | 426/518 |
| 3,528,822 | 9/1970 | Borenstein . | |
| 3,846,566 | 11/1974 | Blomstrom | 426/250 |
| 3,906,112 | 9/1975 | Anderson | 426/250 |
| 4,023,734 | 5/1977 | Herve et al. | 241/17 |
| 4,239,782 | 12/1980 | Cinquemani | 426/2 |
| 4,320,050 | 3/1982 | Rebeller et al. | 426/540 |
| 4,505,936 | 3/1985 | Meyers et al. | 426/540 |
| 4,522,743 | 6/1985 | Horn et al. | 426/540 |
| 4,554,390 | 11/1985 | Curtain et al. | 426/429 |
| 4,726,955 | 2/1988 | Horn et al. | 426/540 |

OTHER PUBLICATIONS

Simpson et al., (1981) in "Carotenoid as Colorants and Vitamin A Precursors", Bauernfiend, ed. pp. 463-538, Academic Press, NY, N.Y.
Nakazoe and Hata (1978) Proc. Jpn. Soc. Sci. Fish., 53rd Meet. Tokyo, Abstract No. 558.
Pringsheim (1966) Phycol. 2:1-7.
Droop (1955) Arkiv. fur Mikrobiologie 21:267-272.
Goodwin and Jamikorn (1954) J. Biochem. 57:376-381.
Droop (1955) Nature 175:42.
Donkin (1976) Phytochemistry 15:711-715.

*Primary Examiner*—R. B. Penland
*Attorney, Agent, or Firm*—Townsend and Townsend

[57] ABSTRACT

Pigment compositions useful for supplementing marine animal feeds comprise comminuted Haematococcus cells treated to degradation of carotenoids, typically by coating or by combination with an anti-oxidant. Encysted Haematococcus cells are ground at cryogenic temperatures, typically by combining the cells with liquid nitrogen in a suitable impact mill. The resulting powder has an average particle size below about 5 $\mu$m. Usually, the Haematococcus will be grown in large-scale culture ponds under controlled conditions.

27 Claims, 1 Drawing Sheet

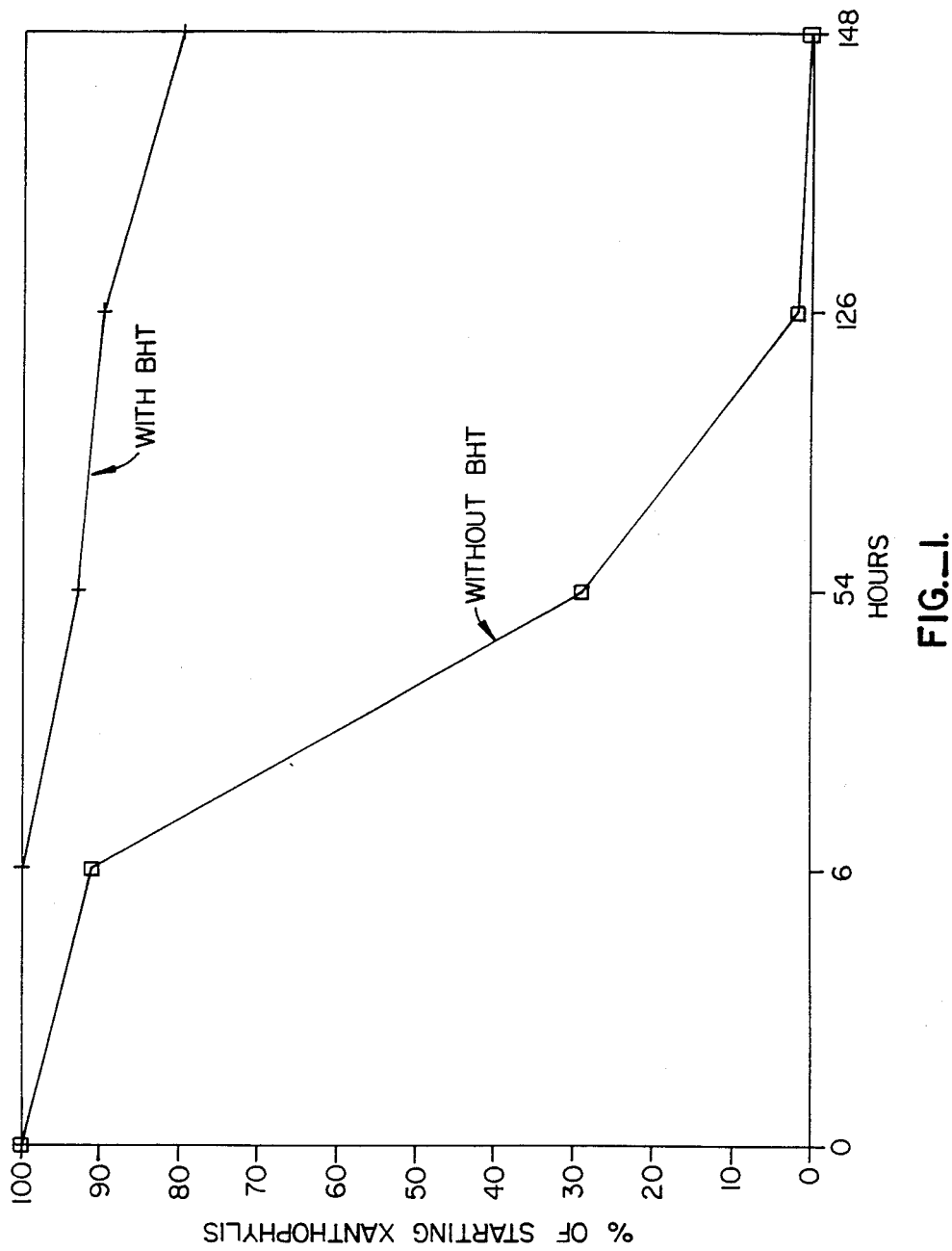

PIGMENTATION SUPPLEMENTS FOR ANIMAL FEED COMPOSITIONS

BACKGROUND OF THE INVENTION

1. Field of the Invention

The present invention relates generally to pigmentation supplements for animal feed compositions, and more particularly to the use of comminuted Haematococcus alga as a pigmentation supplement in compositions for feeding aquatic and other animals.

The cultivation of marine animals, including fish, crustaceans, and the like has become increasingly important with the over-harvesting of natural marine habitats and the growth of the world consumption of these animals. As this cultivation is typically performed in limited areas, such as isolated ponds and estuaries, and at high population densities, it is necessary to provide artificial food sources to supplement whatever natural food sources may be present. To the extent possible, the artificial food sources should mimic the natural food sources so that the cultivated animal product closely resembles the naturally-harvested animal product.

The present invention is concerned primarily with one aspect of such artificial food sources, i.e., the provision of a pigmentation source for naturally pigmented animals such as salmon, trout, shrimp, lobster, chickens, and the like. Such animals, which generally have yellow, orange, and red pigmentation, derive their natural pigmentation from a variety of carotenoids, such as beta-carotene, canthaxanthin, zeaxanthin, astaxanthin, astaxanthin ester, and the like. Of particular interest in preparing artificial food sources is astaxanthin which provides a source of pigmentation in a wide variety of aquatic animals, often without the need for the animal to biologically convert the astaxanthin to any other form of carotenoid.

While astaxanthins are highly successful in providing a natural-appearing pigmentation in a wide variety of animals, natural astaxanthins are limited in availability and synthetic astaxanthins are difficult and costly to prepare. It would therefore be desirable to provide astaxanthin-containing feed supplements which may be produced in large quantities at relatively low cost. Such feed supplements should be effective in enhancing pigmentation of the animal receiving the supplement, should be free from toxicity, and should be storable for relatively long periods of time.

2. Description of the Background Art

Simpson et al. (1981), in: "Carotenoid as Colorants and Vitamin A Precursors" (Bauernfiend, ed.), pp. 463-538, Academic Press, New York, N.Y., references the incorporation of various carotenoids, including astaxanthins, in fish feeds in order to enhance pigmentation. Nakazoe and Hata (1978) Proc. Jpn. Soc. Sci. Fish., 53rd Meet., Tokyo, Abstract No. 558 (cited in Simpson et al. at page 528), describes the feeding of pressed, cellulase-treated Haematococcus to enhance the coloration of Chrysophyrs major. Although an increase in red coloration was reported, the authors noted that the Haematococcus treatment method required improvement. Pringsheim (1966) Phycol. 2:1–7, describes the nutritional requirements of *Haematococcus pluvialis*. Droop (1955) Arkiv. fur Mikrobiologie 21:267-272, describes the factors governing encystment in Haematococcus pluvialis. The biosynthesis of carotenoids by *Haematococcus pluvialis* is discussed in Goodwin and Jamikorn (1954) J. Biochem. 57:376-381; Droop (1955) Nature 175:42; and Donkin (1976) Phytochemistry 15:711-715.

SUMMARY OF THE INVENTION

According to the present invention, pigmentation supplement compositions comprise comminuted Haematococcus alga prepared by grinding dry encysted Haematococcus at cryogenic temperatures, to an average particle size below about 10 μm. The comminuted particles will usually be treated to inhibit degradation by combination with an anti-oxidant or by various coating processes, such as gel coating, microencapsulation, oil coating, and the like. Such pigmentation supplement compositions have been found to be particularly suitable for incorporation in animal feeds, particularly aquatic animal feeds, in order to enhance pigmentation.

Use of the encysted Haematococcus cells as a feed supplement requires that the cells be effectively fractured in order to provide a digestible product. Cryogenic grinding is superior to other comminution methods, such as enzyme treatment, which require separate wash and dry steps to remove enzyme from the product and which potentially leave an enzyme residue in the final product. The present invention, in contrast, allows preparation of final product in a single grinding step which does not require chemical or enzymatic treatment. The anti-degradation treatment allows for storage of the product, even over relatively prolonged periods when exposed to oxygen and light, without substantial degradation of the carotenoids. The comminuted Haematococcus cells can also serve as a source for extracted and purified carotenoids, particularly astaxanthin.

BRIEF DESCRIPTION OF THE DRAWING

FIG. 1 is a graph illustrating the comparative loss of xanthophyll between a sample containing an anti-oxidant and one not containing an anti-oxidant.

DESCRIPTION OF THE SPECIFIC EMBODIMENTS

The feed compositions of the present invention are prepared from encysted algal cells of the genus Haematococcus. The genus Haematococcus consists of flagellated unicellular members of the green algae (Chlorophyceae). The diagnostic characteristic distinguishing members of this genus from other members of the order Volvocales is the cell wall. In flagellated cells, the wall is separated from the plasma membrane, being connected to it only by a series of cytoplasmic strands. Upon encystment, a new cell wall is formed inside the old cell wall. This cell wall thickens and becomes impervious to many types of chemical and physical stresses, making it refractory to conventional grinding techniques. The taxonomy of Haematococcus and its related genera is somewhat indistinct. Haematococcus was for a time referred to as Sphaerella, and differences with members of the genus Chlamydomonas are not always clear. Stephanosphaera is a closely allied genus in which the cells grow in a colonial habit.

All Haematococcus species and strains which produce appreciable amounts of astaxanthins are suitable for use in the present invention. Usually, the amount of astaxanthin produced will be greater than 0.5% by weight of the alga on a dry basis, more usually being at least about 1%, and desirably being 1.5% or greater. Presently, identified species and strains meeting these requirements include H. pluvialis, particularly *H. pluvialis* H1, *H. pluvialis* H2, *H. pluvialis* spitzbergenensis and *H. pluvialis* tvaerminnensis: *H. capensis*, particularly *H. capensis* borealis; *H. droebakensis*, particularly *H. droebakensis* Wollenweber; *H. buetschlii*, particularly *H. buetschlii* Blochmann; and *H. Zimbabwiensis*, particularly *H. zimbabwiensis* Pocock. In addition to these species and strains, Haematococcus is a common organism in nature and isolation of suitable new strains is well within the skill of the art.

Preferred is the use of *H. pluvialis* which is characterized by both rapid growth and proficient production of astaxanthin. Particularly preferred is the use of *H. pluvialis* H2, available from Scripps Institute of Oceanography, La Jolla, Calif.

The strain of Haematococcus selected for production will be maintained in an axenic stock culture with a reserve supply of encysted cells in case the stock culture is lost. A starter culture will be derived by expanding the stock culture in a defined media suitable for algal growth, such as half-strength Bold's basal media, preferably supplemented with thiamine, urea, and sodium acetate. The cells are grown in the stock culture to a density of about $1-5 \times 10^5$ cells/ml under autotrophic or heterotrophic growth conditions. It has been found that low light and low salinity conditions promote rapid expansion of the culture. The culture media should be maintained at a pH in the range from about 6.5 to 8. The starter culture should be expanded until a sufficient volume of inoculum has been obtained for transfer to the production phase, typically in the range from about 50 to 500 L, usually in the range from about 100 to 200 L. Intermediate inoculum cultures may subsequently be grown.

Large-scale production of the Haematococcus will be carried out in a suitable volume of water, typically a lined pool or pond. The volume of the pool or pond is not critical, with larger volumes being consistent with higher production of the alga. Usually, production ponds will have a volume in the range from about 50,000 to 1,000,000 L, more usually in the range from about 30,000 to 500,000 L. The production ponds may be located indoors or outdoors, with indoor locations being advantageous as they limit the potential for introduction of competing microorganisms. Outdoor locations are, of course, much less expensive to provide.

Because of potential contamination, production in open ponds will usually be accomplished by batch procedures. After cleaning and decontaminating, the pond is filled with fresh water, typically of irrigation quality or better. The water will usually be treated with a sterilant, such as chlorine, ozone, or ultraviolet light in order to retard the growth of competing organisms which may be present initially in the water. Suitable nutrients are then introduced to the water. For autotrophic growth, a nitrogen source, such as ammonia or nitrate, and a phosphorus source, such as a phosphate, will usually be sufficient.

Once the nutrients have been supplied to the aqueous production growth media, the inoculum can be added. The volume of the inoculum provided will depend on the volume in the production phase, usually being in the range from about 0.5 to 5% of the production volume, more usually being in the range from about 1 to 2% of the production volume. After the inoculum has been added, the production growth media should be slowly mixed. Carbon dioxide gassing will typically be used to control pH as well as provide inorganic carbon for growth. Maximal growth is obtained when the cells are exposed to relatively low light conditions.

Alternately, heterotrophic cell growth may be achieved (in addition to autotrophic) by supplementing the growth medium with organic carbon sources, nitrogen sources, and vitamins. A variety of organic carbon sources are available, with acetic acid being preferred. Urea is the preferred nitrogen source and thiamine the vitamin. While heterotrophic growth enhances the overall growth rate, such cultures are more susceptible to contaminating microorganisms and it is essential that they be maintained under sterile conditions.

Growth of the production phase will continue until a desired cell density is achieved, typically in the range from about $10^5$ to $10^6$ cells/ml, more typically in the range from about $3 \times 10^5$ to $6 \times 10^5$ cells/ml in autotrophic cultures. Once such a cell density has been reached, encystment of the algal cells will be promoted, typically by nutrient deprivation, an increase in salinity, or both. Nitrogen deprivation and/or salt (NaCl, $CaCl_2$, and the like) concentrations above about 50 mM (0.3% by weight) have been found to promote encystment.

Once encystment has been achieved, the encysted cells may be harvested by cessation of pond mixing, allowing the cells to settle. Thereafter, the paste is heated to a temperature above about 70° C. to dry the cells and kill the cells and any contaminating microorganisms. Optionally, the dried cells may be washed to remove extraneous material. Depending on the purity desired, further cleaning of the encysted cells may be appropriate, such as by washing with dilute acid.

The dried, cleaned Haematococcus cells will be comminuted to form a powder having an average particle size below about 10 μm, preferably being below about 5 μm. Particles in this size range are particularly suitable for incorporation into animal feed compositions, as will be described in more detail hereinafter.

After comminution, the powder will normally be treated to inhibit degradation of the carotenoids which are the desirable components. Conveniently, the particles of the powder may be coated with an edible material to form an oxygen barrier to inhibit oxidation. Numerous suitable gel coating, oil coating, and microencapsulation techniques are described in the patent and scientific literature.

Alternatively, a sufficient amount of a suitable anti-oxidant may be added to inhibit degradation of the carotenoids present in the ground product. Suitable anti-oxidants include butylated hydroxytoluene (BHT), ethoxyquin, tocopherols, butylated hydroxyanisole, di-tert-butyl-paracresol, propyl gallate, and the like. The amount of anti-oxidant will depend on the particular anti-oxidant chosen, typically being in the range from about 0.05 to 5% by weight of the final product, more typically being in the range from about 0.1 to 3% by weight of the final product. The anti-oxidant may be added either before or after comminution of the alga. By adding before comminution, a separate mixing step may be avoided.

As a second alternative, the comminuted Haematococcus cells may be packaged in a manner which inhibits oxidation, such as vacuum packing or packing with oxygen absorbers. Such packing is not preferred, however, since the product will degrade as soon as the packaging is opened.

As the cell wall of the encysted Haematococcus cells is refractory to conventional grinding techniques, the method of grinding is critical to the present invention. The cells must be dry, in order to allow fracturing by high speed impact mills and jet mills. It has been found that grinding under cryogenic conditions, typically at a temperature below about −50° C., more typically at a temperature below about −170° C., is greatly facilitated and provides a highly uniform and well-preserved product.

Conveniently, the encysted Haeomatococcus cells may be combined with a cryogenic liquid, such as liquid nitrogen, before grinding. One particularly suitable grinding apparatus is an impact mill manufactured by Vortec Products, Long Beach, Calif. The Vortec impact mill allows for simultaneous introduction of both the encysted Haematococcus cells and liquid nitrogen so that the cells are cooled below the desired temperature during the grinding procedure. After grinding, the liquid nitrogen sublimates, leaving a dry final product.

The pigment compositions of the present invention will include a variety of pigments derived from the Haematococcus cells. The pigments include astaxanthin esters, alpha-carotene, beta-carotene, lutein, violoxanthin, neoxanthin, chlorophyl a, chlorophyl b, and free astaxanthin, as well as trace amounts of lutein epoxide, zeaxanthin, antheraxanthin, echinenone, canthaxanthin, and various keto-carotenoids. Astaxanthin esters are the primary pigment in *Haematococcus pluvialis* cysts, typically ranging from 60% to 80% by weight of the total pigment content. The astaxanthin content of the pigment composition will typically be at least about 0.5% by weight based on the total product weight, usually being in the range from about 1% to 2% of the total product weight.

The pigment compositions of the present invention will usually be combined in a feed composition formulated for the animal to be fed. Such formulations typically include grains, such as wheat, alfalfa, soybean, and rice flours; fish meals; shrimp meals; as well as vitamin and oil supplements. A wide variety of formulations are reported in both the patent and scientific literature.

The pigmentation compositions of the present invention may be added to such conventional feed compositions, typically at a concentration in the range from about 10 to 200 ppm, more usually in the range from about 25 to 100 ppm. Such formulations may then be fed to the animals by conventional techniques.

Aquatic animals which may benefit from receiving feed compositions supplemented with the pigment composition of the present invention include fish (pisces), such as salmon, trout, and pigmented carp; crustaceans, such as shrimp, prawns, lobster and crab. Other animals having a desirable yellow or orange pigmentation, such as chickens, may also benefit from the feed compositions of the present invention.

The comminuted Haematococcus can also serve as a source of extracted and purified carotenoids, particularly astaxanthin, which may find use in food supplements, colorants, and the like. Carotenoids may be extracted from the comminuted Haematococcus by conventional extraction techniques using suitable organic solvents, including oils; aromatics, e.g., benzene; halogenated hydrocarbons, e.g., methylene chloride; alkanes, e.g., hexane, and the like. The comminution process of the present invention is critical in obtaining improved yields of carotenoids from Haematococcus. Conveniently, edible oils such as vegetable oils, may be used for extraction and the resulting product may be used directly as a feed supplement with minimal or no further processing. The comminuted cells are mixed with the solvent, and the resulting liquid phase containing the total lipid fraction (including the carotenoids) separated by filtration.

The extracted carotenoids, particularly astaxanthin, may also be further purified by conventional techniques, such as adsorption, chromatography, solvent-solvent extraction, crystallization, and the like. Usually, the desired purity will be at least about 50% by weight, more usually be at least about 75% by weight, and frequently being at least about 90% by weight, and above.

The following examples are offered by way of illustration and not by way of limitation.

EXPERIMENTAL

Described below are procedures for outdoor autotrophic growth of Haematococcus pluvialis H2 and subsequent production of final product. Inoculum Bacteria-free, unialgal stock cultures are maintained in medium with the following composition:

| Component | Concentration |
| --- | --- |
| Sodium chloride | 12.5 mg/l |
| Calcium chloride | 12.5 mg/l |
| Magnesium sulfate | 38 mg/l |
| Potassium phosphate dibasic | 93 mg/l |
| Potassium phosphate monobasic | 44 mg/l |
| Sodium ethylene diamine tetraacetic acid (EDTA) | 25 mg/l |
| Ferric chloride | 2.5 mg/l |
| Sodium molybdate | 0.35 mg/l |
| Zinc sulfate | 4.4 mg/l |
| Manganese chloride | 0.73 mg/l |
| Copper sulfate | 0.77 mg/l |
| Cobalt chloride | 0.23 mg/l |
| Thiamine | 4.1 mg/ml |
| Sodium acetate | 1.4 g/l |
| Urea | 0.12 g/l |

The medium is made up in deionized water and adjusted to pH 7.3. If solid medium is desired, 1.5% agar is added before autoclaving.

The starting inoculum cultures are green, vegetative, swimming cells grown axenically in successively larger flasks until approximately the 2 liter stage. As inoculum is transferred to 10 and 200 liter clear plastic vessels for larger scale growth, the sodium acetate is no longer added to the medium and 101 mg/liter sodium nitrate is substituted for the urea. Beyond this growth stage, all of the cultures are autotrophic. Up to approximately the 200 liter stage, cultures are maintained in controlled indoor conditions. Sixteen hours of light are provided each day from cool white fluorescent bulbs ($1.2 \times 10^{16}$ quanta/sq cm-sec). Light period temperatures are kept at approximately 30° C. and dark temperatures at 25° C. Carbon dioxide is supplied on demand to maintain pH at approximately 7.3. At each stage cultures are grown up to a density of approximately $2 \times 10^5$ cells per ml.

Beyond the 200 liter stage, inoculum cultures are grown as swimming cells in outdoor ponds. The outdoor medium is made with irrigation water disinfected by filtration, chlorination, ozonation, or ultraviolet light. To this water are added 1.0 mM ammonium bicarbonate, 0.4 mM potassium phosphate dibasic, 0.02 mM ferric chloride, 0.01 mM EDTA, and 0.025 mM magnesium sulfate. The outdoor culture containments are low-walled and have a center divider. They are lined with white plastic. A paddlewheel at one end produces slow circular mixing of the culture. Culture depth is 12 to 15 cm. With sufficient inoculum (above $10^4$ cells/ml) the cultures are able to grow in full sunlight as vegetative cells. Lower light is optimal, however, and young cultures can be enhanced by covering the ponds with screening material. Contamination with other algae, fungi and protozoa from the environment is a very significant problem in outdoor cultures. Cultures are grown as fast as possible in the swimming phase with carbon dioxide supplied on demand to maintain pH at 7.3. The cells will be mostly green with a varying amount of astaxanthin apparent in the central region of each cell. Each culture is grown in a batch mode with cleaning of the liner between cultures to avoid contamination carryover. Outdoor inoculum cultures are grown up to a cell density of approximately $3 \times 10^5$ cells/ml before transfer. Under optimal temperature conditions they can grow from an inoculum of $2 \times 10^4$ to $3 \times 10^5$ in approximately 5 days. Outdoor inoculum growth is in successive cultures of 5,000 and 50,000 liter.

PRODUCTION GROWTH

Production cultures are 3 to $5 \times 10^5$ liters. They are started and grown in the manner of the inoculum cultures described above. If left to mature (grown beyond about 5 days) such a culture will naturally start to encyst. Just before and continuing through the process of encystment, the cell contents will become increasingly filled with the red astaxanthin pigments. Mature cysts will tend to settle out even while the paddlewheel is mixing. Approximately 10 days after inoculation in an optimal culture, all of the cells will be non-motile, thick walled and fully red. They are then ready for harvest. The encystment and astaxanthin formation process can be facilitated by several adjustments to the medium. Nitrogen or another key nutrient can be allowed to become exhausted. In addition, the salinity of the medium can be raised either through natural evaporation or through the addition of sodium chloride.

HARVEST AND DRYING

The harvest method used takes advantage of the fact that mature red cysts have a density significantly greater than water. With the paddlewheel turned off, the cysts settle to the bottom of the pond within approximately one hour. The medium on top is then pumped off, resulting in an initial reduction in volume of about 80%. The cysts are further concentrated before drying. Centrifugation is a convenient means of accomplishing this. Since the cysts are quite dense and resistant to mechanical damage, many types of continuous flow centrifuges will work well. The resulting algal paste is next usually heated to approximately 70° C. to kill the Haematococcus as well as any contaminating cells. The paste is next taken to near dryness (10% water or less) before grinding. Several types of conventional dryers, such as spray dryers, vacuum drum dryers, or tray dryers, were used successfully. Conditions of high temperature, high oxygen concentration and high light are to be avoided during drying to prevent pigment degradation.

GRINDING

Anti-oxidant (2% butylated hydroxytoluene or 2% ethoxyquin) is added to the dry algae. Using an insulated screw-type solids feeder, liquid nitrogen is combined with the algae cells just before they are fed into a Vortec Products Company M1 impact mill. The temperature reading at the inlet port reads between $31$ -$170°$ C. and $-184°$ C. The impact mill is set to operate at maximum speed of 20,000 rpm. Flow rates can be as high as 1.5 kg per minute. Dry ground product emerges from the mill. Due to clumping of the cells, a second pass of grinding with the same conditions is run to assure that virtually all of the cells are broken. The fine powder emerging from this second pass is final product.

FISH FEED FORMULATION

The red powder was assayed for xanthophyll content by extraction of a sample with organic solvents and spectrophotometric reading. Total xanthophyll levels between 1.0% and 2.5% are normal. The red powder may be combined with an edible powder, such as wheat flour, in order to provide a product having a consistent xanthophyll content, e.g., 1.0%. Xanthophyll levels of between 20 and 50 ppm have been used in blending fish feed for feeding trials. Successful natural orange-pink coloration of Coho salmon, sea bream and koi carp has been achieved in feeding trials. The pigmentation has been as good or better than that obtained by the addition of synthetic astaxanthin or synthetic canthaxanthin.

DEGRADATION OF XANTHOPHYLLS

Equal portions of the red powder were obtained, with one such portion being free from anti-oxidant (BHT) and the other containing about 1% BHT. The samples were exposed to the ambient at room temperature and under fluorescent light for 148 hours. Xanthophyll content was measured at 0, 6, 54, 126, and 148 hours. The results are set forth in FIG. 1. It can be seen that the use of an anti-oxidant is necessary for long term stability of the product when exposed to air.

Although the foregoing invention has been described in some detail by way of illustration and example for purposes of clarity of understanding, it will be obvious that certain changes and modifications may be practiced within the scope of the appended claims.

What is claimed is:

1. A pigmentation supplement composition consisting essentially of comminuted Haematococcus alga having an average particle size below about 10 μm, wherein the Haematococcus was comminuted while in the dried encysted state said composition also containing a degradation inhibiting material.

2. A pigmentation supplement composition as in claim 1, wherein the Haematococcus species is *H. pluvialis, H. capensis, H. droebakensis, H. buetschlii,* and *H. zimbabwiensis.*

3. A pigmentation supplement composition as in claim 1, wherein the comminuted Haematococcus alga has been combined with an anti-oxidant to inhibit degradation.

4. A pigmentation supplement composition as in claim 3, wherein the anti-oxidant is selected from the group consisting of butylated hydroxytoluene (BHT), ethoxyquin, tocopherols, butylated hydroxyanisole, di-tert-butyl-paracresol, and propyl gallate.

5. A pigmentation supplement composition as in claim 1, wherein the comminuted Haematococcus alga has been coated or microencapsulated to inhibit degradation.

6. A method for preparing a carotenoid composition, said method comprising:

chilling dried encysted Haematococcus cells to a cryogenic temperature below about $-50°$ C.; and comminuting the chilled cells at said cryogenic temperature to obtain particles having an average size below about 10 μm.

7. A method as in claim 6, further comprising treating the comminuted Haematococcus cells to inhibit degradation of the carotenoids in the particles.

8. A method as in claim 7, wherein the comminuted Haematococcus cells are combined with an anti-oxidant.

9. A method as in claim 8, wherein the comminuted Haematococcus cells are combined with the anti-oxidant prior to comminuting.

10. A method as in claim 8, wherein the comminuted Haematococcus cells are combined with the anti-oxidant subsequent to comminuting.

11. A method as in claim 8, wherein the anti-oxidant is selected from the group consisting of butylated hydroxytoluene (BHT), ethoxyquin, tocopherols, butylated hydroxyanisole, di-tert-butyl-paracresol, and propyl gallate.

12. A method as in claim 7, wherein the comminuted Haematococcus cells are coated by a gel.

13. A method as in claim 7, wherein the comminuted Haematococcus cells are coated with an oil.

14. A method as in claim 7, wherein the comminuted Haematococcus cells are microencapsulated.

15. A method as in claim 6, wherein the Haematococcus cells are chilled by exposure to liquid nitrogen.

16. A method as in claim 15, wherein the Haematococcus cells are comminuted in an impact mill while being simultaneously exposed to liquid nitrogen.

17. A method as in claim 6, wherein the Haematococcus species is selected from the group consisting of *H. pluvialis, H. capensis, H. droebakensis, H. buetschlii,* and *H. zimbabwiensis.*

18. A method for enhancing the pigmentation of animals having yellow, orange or red pigmentation, said method comprising:

feeding the animal a composition comprising comminuted Haematococcus alga having an average particle size below about 10 μm, wherein the Haeomatococcus was comminuted at a cryogenic temperature while in the dried encysted state.

19. A method as in claim 18, wherein the comminuted Haematococcus alga has been combined with an anti-oxidant to inhibit degradation.

20. A method as in claim 19, wherein the comminuted Haematococcus alga has been coated or microencapsulated to inhibit degradation.

21. A method as in claim 18, wherein the Haematococcus species is selected from the group consisting of *H. pluvialis, H. capensis, H. droebakensis, H. buetschlii,* and *H. zimbabwiensis.*

22. A method as in claim 18, wherein the anti-oxidant is selected from the group consisting of butylated hydroxytoluene (BHT), ethoxyquin, butylated hydroxyanisole, di-tert-butyl-paracresol, and propyl gallate.

23. A process for extracting carotenoids from Haematococcus alga, said process comprising contacting dried encysted Haematococcus cells comminuted at a cryogenic temperature with an organic solvent to form a solid phase and a liquid phase; and separating the liquid phase which contains the solubilized carotenoids.

24. A process as in claim 23, wherein the organic solvent is selected from the group consisting of oils, aromatics, hydrocarbons, and halogenated hydrocarbons.

25. A process as in claim 24, wherein the organic solvent is an edible oil.

26. A process as in claim 23, wherein the Haematococcus cells have been comminuted at a temperature below about −50° C.

27. A process as in claim 23, further including purification of an astaxanthin fraction from the liquid phase to a purity of at least about 50% by weight.

* * * * *